(12) United States Patent
Stanley, III

(10) Patent No.: US 6,660,047 B1
(45) Date of Patent: Dec. 9, 2003

(54) METHOD OF FORMULATING A HAIR COLORING COMPOSITION

(76) Inventor: Virgil E. Stanley, III, 5860 N. Michigan Rd., Indianapolis, IN (US) 46228

(*) Notice: Subject to any disclaimer, the term of this patent is extended or adjusted under 35 U.S.C. 154(b) by 0 days.

(21) Appl. No.: 10/138,199

(22) Filed: May 3, 2002

Related U.S. Application Data

(62) Division of application No. 09/893,819, filed on Jun. 28, 2001, now Pat. No. 6,440,175.

(51) Int. Cl.[7] ............................................. C09B 67/00
(52) U.S. Cl. .................. 8/527; 8/636; 8/638; 132/202; 132/207; 132/208; 132/212; 132/221; 424/400; 424/401; 424/70.1; 424/70.6
(58) Field of Search ..................... 8/527, 638, 636; 132/202, 207, 208, 212, 221; 424/400, 401, 70.1, 70.6

(56) References Cited

U.S. PATENT DOCUMENTS 5,862,947 A * 1/1999 Wiegner et al. .............. 222/82

* cited by examiner

Primary Examiner—Yogendra N. Gupta
Assistant Examiner—Eisa Elhilo
(74) Attorney, Agent, or Firm—Coats & Bennett, P.L.L.C.

(57) ABSTRACT

The present invention entails a hair coloring kit that enables a person to mix or formulate a plurality of different hair color compositions. The kit includes a base composition or hair spray, a group of color concentrates, and a dispenser. One or more of the color concentrates is mixed with the base composition in the dispenser to form a hair coloring composition of a particular color. Thereafter, the formed hair coloring composition can be sprayed onto the hair of a person.

7 Claims, 1 Drawing Sheet

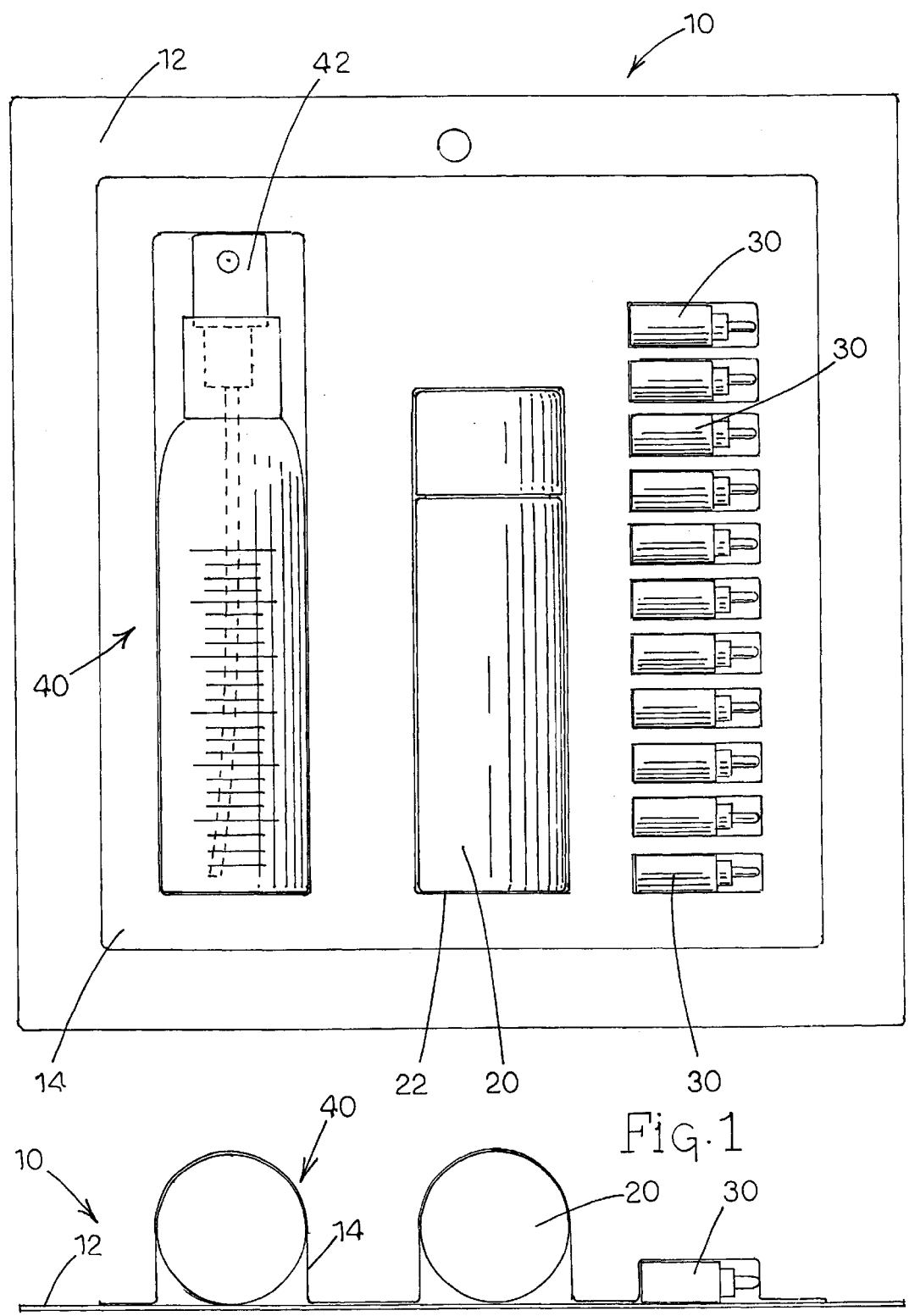

METHOD OF FORMULATING A HAIR COLORING COMPOSITION

This is a divisional of application Ser. No. 09/893,819, filed Jun. 28, 2001, now U.S. Pat. No. 6,440,175.

FIELD OF THE INVENTION

The present invention relates to hair coloring compositions, methods of forming hair coloring compositions, and methods of applying hair coloring compositions. More particularly the present invention relates to a hair coloring kit that enables a person to mix and form hair coloring compositions of many colors.

BACKGROUND OF THE INVENTION

In recent years it has become popular and even perhaps fashionable to color one's hair in vibrant colors. In fact, it is not unusual to find children, young adults and older adults coloring their hair multicolors. In many instances, these uses of hair coloring are only temporary, and in some cases such hair coloring is simply a short term artistic expression or sometimes individuals are inspired to color their hair because of the feeling or feelings that result. In this regard, it is not uncommon to see students at various universities at athletic events with their hair colored in university colors.

These types of hair coloring compositions are intended to be utilized for short terms such as one day or less. Such hair coloring compositions may be in various forms. For example, some of the more popular hair coloring compositions that are used by students and even small children during Halloween are of an aerosol type. In such cases, a person can simply spray his or her hair a particular color. When that person is ready to return to his or her normal color, the hair coloring composition can simply be washed from the hair.

As noted above, the trend in temporary hair coloring applications has tended to be towards the application of multicolors, sparkles or glitter. However, consumers desiring to apply multicolors to their hair are forced to purchase a separate bottle or container of hair coloring for each desired color. This can be expensive especially in light of the fact that these types of hair coloring compositions are not routinely used and it is not uncommon for a consumer to use only small amounts of a particular hair coloring composition over a substantial period of time.

Therefore, there has been and continues to be a need for a hair coloring kit that will serve this market and which will permit a person to mix or formulate a wide variety of different hair coloring compositions. It is contemplated that such a kit would be relatively inexpensive and would permit a consumer to have the ability to color their hair in a wide variety of colors without having to purchase conventional containers of hair coloring compositions.

SUMMARY OF THE INVENTION

The present invention entails a hair coloring kit that enables a consumer to mix or formulate a variety of different hair color compositions. The kit includes a group or set of color concentrates. A container of a base composition is also provided. One or more of the color concentrates is mixed with the base composition in a dispenser. Once the color composition is mixed in the dispenser, the color composition is dispensed onto a person's hair. The group of color concentrates can take various forms. The different color concentrates may be in the form of tablets, powders, or a series of liquids.

BRIEF DESCRIPTION OF THE DRAWINGS

FIG. 1 is a planned view of the hair coloring kit of the present invention.

FIG. 2 is an end elevational view of the hair coloring kit of the present invention.

DETAILED DESCRIPTION OF THE INVENTION

With further reference to the drawings, the present hair coloring kit is shown therein and indicated generally by the numeral 10. The hair coloring kit 10 is designed to be incorporated into one package. While the kit may, on the other hand, be placed in more than one package it is contemplated that in one embodiment, the components of the kit would be placed on a header card 12 and basically contained by a blister cover 14. The header card 12 can be provided with colorful graphics and indicia that may incorporate a trademark and logo as well as directions for use of the hair coloring kit. For example, a color or tone chart, such as a Pantone chart, may be provided which will direct the consumer on how to mix two or more colors together to achieve a particular color, shade or tone. As will be discussed later herein, the hair coloring kit 10 includes a number of components and these components may be appropriately secure to the header card 12. A number of securing means may be utilized in conjunction with the header card 12 to secure the various components to the card 12. In the way of a number of examples, the header card 12 can be provided with a series of recesses formed in the card. The individual components of the kit 10 can be placed in the individual recesses and contained therein by the blister cover 14. Additionally, elastic bands or other types of stretchable securing means can be incorporated into the header card 12 such that the respective elastic bands will partially encircle and hold the individual components adjacent the header card 12. In short, various types of securing means can be incorporated into the header card 12 for securing the individual components of the kit to the header card 12 and within the package itself.

Now turning to the components of the hair coloring kit 10, it is seen that the kit includes a base composition 20. This base composition 20 is contained within a container 22 that again is secured and held to the header card 12. Various types of base compositions can be used. The principal function of the base composition is to mix with one or more color concentrates or color constitutes to form a particular hair color composition. It is contemplated, that the base composition can simply be a conventional hair spray such as a conventional styling hair spray that is utilized to hold the hair of a person in place. Another example of the base composition would entail a tablet or powder that could be mixed with water to form the base. In any event, as alluded to above, the base composition or hair spray is adapted to be mixed with a coloring composition such as a color concentrate or a color constitute.

The kit 10 also includes a group or set of color compositions. These color compositions can assume various forms. It is expected that the group or set of color compositions provided with the kit 10 will include a variety of different color concentrates or different color compositions. For example, it is contemplated that the color compositions provided would include the colors green, yellow, blue, red, orange, brown, white, black or any other colors such as purple or any other shades or variations of these colors. In addition, the colors may include glitter or sparkles.

As noted above, these color compositions can be provided in different forms. In one embodiment these color compositions or color concentrates can simply be in the form of liquids. That is, there would be provided a separate container or vial for each different color composition or color concentrate. These vials or containers are referred to by the numeral 30 in the drawings. In the case of the embodiment shown in FIG. 1, there is shown ten different vials or containers 30. Each vial can be provided with a medicine dropper, syringe or eye dropper for transferring the color concentrate from a respective container 30 such that the color concentrate can be mixed with the base composition. Other types of transfer devices can be utilized. In fact, the respective containers or vials may simply be provided with a cap and in the process of mixing a color composition or a color concentrate with the base solution, the color concentrate is simply poured from the respective vials or containers.

In addition to providing the color concentrates in the form of a liquid, these color concentrates can be provided in the form of a tablet, powder or jell. In the case of a tablet, there would be provided one or more tablets for each desired color. These tablets could be contained in individual recesses provided in the header card 12 or could be packaged in individual containers or packages themselves. Another possible form for the color concentrate would be powder. That is, each color concentrate or color composition could be in the form of a small container of a powder. That is, there would be a blue powder, red powder, green powder and so forth and so on. These tablets or powders would be dissolved in the base composition to give rise to a particular color.

In addition to the color concentrates just described, the kit 10 of the present invention is provided with a dispenser indicated generally by the numeral 40. Dispenser 40 serves a number of functions. First, it serves as the mixing container for mixing the base composition 20 with one or more of the color concentrates just described. The second function that the dispenser 40 performs is dispensing the formulated or mixed hair colored solution onto a person's hair. In any event, the dispenser 40 comprises a container such as a small plastic bottle that, for example, could hold between 2 and 8 ounces of fluid. In the case of the embodiment illustrated in FIG. 1, the dispenser 40 includes a number of graduated volume lines. These graduated volume lines will assist the consumer or user in appropriately mixing the color concentrates 30 with the base composition 20.

Dispenser 40 also includes a pump 42. Pump 42 is adapted to be screwed onto a top of the dispenser and includes a feed line extending downwardly from the pump into the dispenser 40. Pump 42 is of a conventional design such as the type that is customarily used in connection with hair sprays. The pump 42 includes a finger or thumb actuator that is pressed downwardly in repeating fashion and in the process creates a pumping action that pumps the hair coloring composition from the container and dispenses the hair coloring composition through a spray nozzle that forms a part of the pump 42. It should be appreciated that other types of dispensers can be utilized.

In use, a person will pour a certain volume of the base composition 20 into the dispenser 40. Depending upon the color of the hair coloring composition desired, the individual will select one or more of the individual color concentrates that are provided with the kit 10. In many instances, an individual may simply want a single color for the hair coloring composition. In those cases, a single color concentrate will be selected or in some cases two or more color concentrates can be selected so as to yield one color that is arrived at as a result of the color concentrates being mixed or blended together in the base composition. It is contemplated that a set of directions or instructions, such as a Pantone chart, accompanying the kit 10 would provide guidance to consumers and people using the kit 10 and these instructions and guidance would enable the users of the kit 10 to arrive at certain colors. Once the one or more color concentrates have been placed in the dispenser 40 along with the base composition 20, the dispenser 40 can be subjected to a shaking action. This shaking action will cause the one or more color concentrates to dissolve within the base composition and to mix therewith to yield a particular color. Thereafter, the pump 42 or other applicator is actuated causing the color composition to be pumped from the dispenser onto the hair of the person using the kit 10. In some situations, a user might prefer coloring one portion of his or her hair one color and another portion of his or her hair another color. In these cases, the dispenser 40 would be cleaned after a first use and thereafter the second desired color could be mixed within the dispenser 40 and applied to a separate area of the user's hair.

The hair colorant or concentrates used in formulating the various color hair compositions can vary quite widely depending on the nature of the results desired. For the most part, the formulated or mixed hair coloring composition will be temporary hair coloring compositions. The hair colorants or concentrates used can be of the direct dye variety, that is colorants that do not require oxidizing agents to develop their color. A large number of hair colorants are known in the prior art that can be used in the practice of this invention.

The quantity of colorant or concentrate that may be contained in a final hair coloring composition may vary. For a more complete and unified understanding of hair colorants and hair coloring compositions, one is referred to the disclosures found in U.S. Pat. Nos. 4,873,079; 5,613,985; 2,983,651; 3,402,986; 3,649,102; 3,480,377; 3,632,920; and 1,159,331. The contents and disclosures of all of these patents are expressly incorporated herein by reference.

There are many advantages to the present invention. By purchasing a single kit, one will have the ability to formulate a wide variety of hair colors. Thus, to achieve a multi-color look or to use a series of single colors over an extended time period, the consumer will not be required to purchase, if even available, a plurality of different hair coloring compositions in the conventional sense. The single kit of a present invention will provide all of those options. In addition, the kit of the present invention offers advantages to the retailer as well. By stocking the kit of the present invention, retailers will be able to offer an unlimited variety of colors yet minimize the shelf space required.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A method of formulating a hair coloring composition comprising: selecting one or more color concentrates from a group of color concentrates and mixing the one or more color concentrates with a base composition wherein said base composition is contained within a container and wherein the mixing includes pouring the base composition into a disperser and mixing one or more color concentrates with the base solution within the disperser to form the hair coloring composition.

2. The method of claim 1 wherein the group of color concentrates and the base composition form a part of a hair coloring kit that enables a person to form hair coloring compositions of different colors.

3. The method of claim 1 wherein the base composition includes a hair spray composition that when mixed with one or more color concentrates forms a hair coloring spray that may be sprayed onto a person's hair.

4. The method of claim 1 wherein the group of hair coloring concentrates are in a form taken from the group of tablets, powders and liquids.

5. The method of claim 1 wherein the dispenser includes a spray pump for spraying the formed color composition from the dispenser onto a person's hair.

6. The method of claim 1 wherein the formulated hair coloring composition is formed by mixing two or more color concentrates with the base composition.

7. The method of claim 1 including mixing the one or more color concentrates with the base composition in a dispenser that includes a spray pump; and pumping the formulated hair coloring composition from the dispenser onto the hair of a person.

\* \* \* \* \*